US00PP15240P3

(12) United States Plant Patent
Hansen

(10) Patent No.: US PP15,240 P2
(45) Date of Patent: Oct. 19, 2004

(54) MINIATURE ROSE PLANT 'EVERGREEN'

(50) Latin Name: *Rosa hybrida*
Varietal Denomination: EVERgreen

(76) Inventor: Rosa Eskelund Hansen, Stationsvej 51, Faaborg DK 5600 (DK)

( * ) Notice: Subject to any disclaimer, the term of this patent is extended or adjusted under 35 U.S.C. 154(b) by 101 days.

(21) Appl. No.: 10/098,209

(22) Filed: Mar. 18, 2002

(65) Prior Publication Data

US 2003/0177549 P1 Sep. 18, 2003

(51) Int. Cl.[7] ..... A01H 5/00
(52) U.S. Cl. ..... Plt./118

(58) Field of Search ..... Plt./117, 118, 116

(56) References Cited

U.S. PATENT DOCUMENTS

PP11,146 P * 12/1999 Kordes ..... Plt./125

* cited by examiner

*Primary Examiner*—Howard J. Locker

(57) ABSTRACT

A new miniature rose plant which has abundant, long lasting, warm yellow-lime colored flowers and attractive foliage. The variety successfully propagates from softwood cuttings and is suitable for year round production in commercial glass houses as a flowering pot plant. This new and distinct variety has shown to be uniform and stable in the resulting generations from asexual propagation.

2 Drawing Sheets

Figures 1, 2, 3, 4, 5, 6, 7, 8, 9:
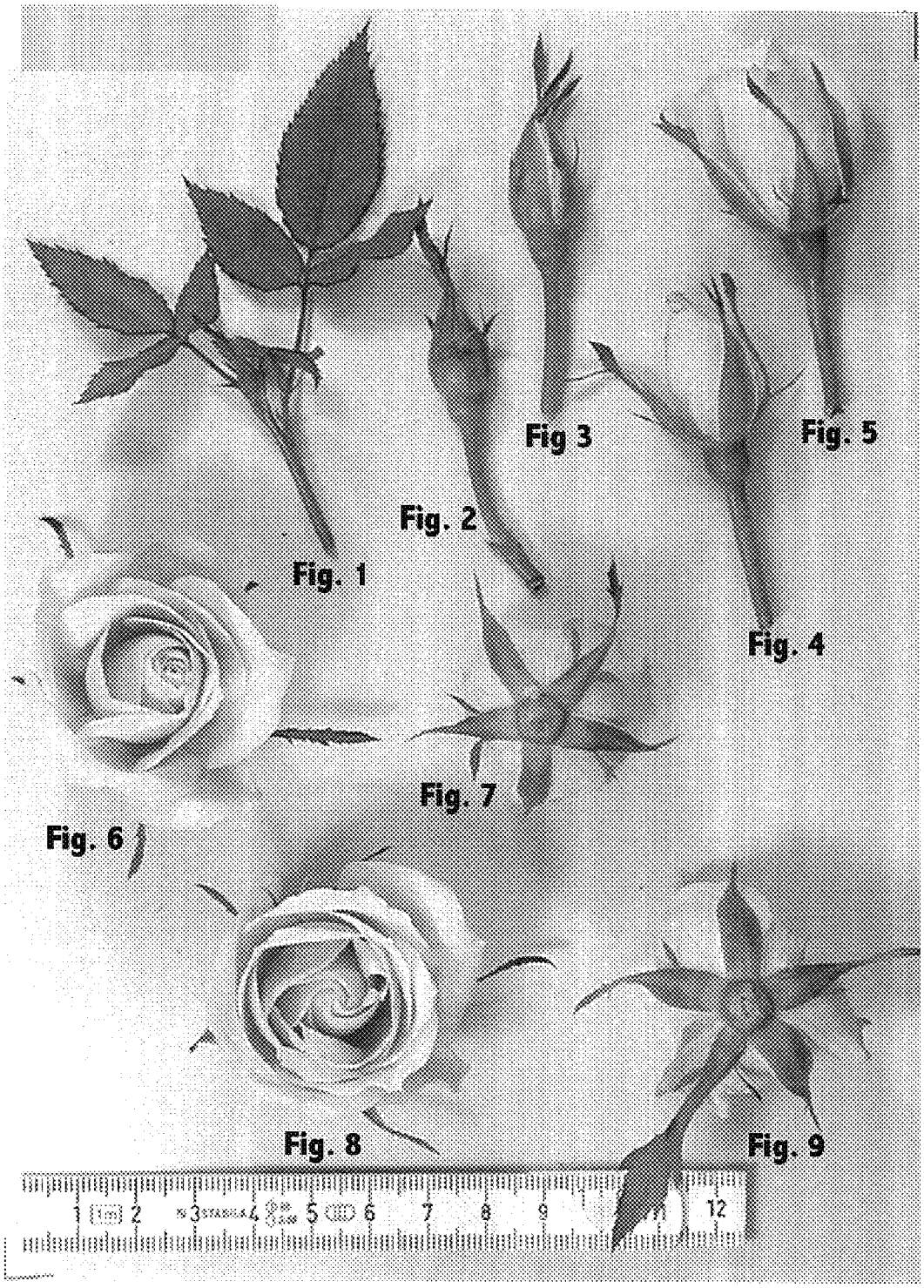

Latin name of genus and species: *Rosa hybrida* 'EVERgreen'.

Variety denomination: The new variety is named 'EVERgreen'.

BACKGROUND OF THE INVENTION

The present invention constitutes a new and distinct variety of miniature rose plant, which was developed by artificially pollinating an unnamed seedling(not patented in the US) with an unnamed seedling (not patented in the US). The two parents were crossed in the summer of 2000 and the resulting seed was sown in December 2000, in a controlled glasshouse environment. Out of these seedlings one seedling was selected, as the new variety and named 'EVERgreen'. The new rose may be distinguished from its seed parent, an unnamed seedling, by the following combination of characteristics:

1. The unnamed seedling has a breeding background in unnamed seedlings.
2. 'EVERgreen' has big double flowers, while the unnamed seedling has big single flowers.
3. 'EVERgreen' has yellow-lime colored petals, while the unnamed seedling has pale yellow petals.

The new variety may distinguished from its pollen parent, an unnamed seedling created by the same inventor, by the following combination of characteristics:

1. The unnamed seedling has a breeding background in unnamed seedlings.
2. 'EVERgreen' has bigger flowers and foliage as compared to the unnamed seedling.
3. 'EVERgreen' has yellow-lime colored petals, while the unnamed seedling has light pink petals.

BRIEF SUMMARY OF THE INVENTION

Initial asexual reproduction of 'EVERgreen' by cuttings was first done in a controlled greenhouse environment in Faaborg, Denmark. This and subsequent asexual reproductions of the plant in controlled greenhouse environments have proven that the foregoing and all other distinctive and characteristic features of the plant come true to form and are firmly fixed through asexual propagation in resulting generations. 'EVERgreen' is a low and compact miniature rose with medium vigor. The shelf life for the plant and for a single flush of bloom has been tested to be medium.

The objective of the hybridization of this rose variety for commercial greenhouse culture was to create a new and distinct variety with:

1. Uniform and abundant flowers with good keepability;
2. Attractive long lasting foliage and compact growth, and young foliage has striking red edges;
3. Year round flowering under glasshouse conditions;
4. Suitability for production from softwood cuttings in pots;
5. Durable flowers and foliage which make the variety suitable for distribution in the floral industry.

This combination of qualities was not present in previously available commercial cultivars of this type and distinguish 'EVERgreen' from all other varieties of which we are aware. The seeds from hybridization were planted in a controlled environment and evaluations were conducted on the resulting plants. 'EVERgreen' was selected by, Rosa Eskelund Hansen, in his development program in Faaborg, Denmark.

BRIEF DESCRIPTIONS OF THE DRAWINGS

The accompanying color illustrations show as true as is reasonably to obtain in color photographs of this type, the typical characteristics of the buds, flowers, leaves, stems of 'EVERgreen'. Specifically illustrated in:

Photo sheet #1:

FIG. 1 Young shoot.

FIG. 2 Bud before opening the sepals.

FIG. 3 Bud at the stage opening the sepals.

FIG. 4 Bud at the stage opening the petals.

FIG. 5 Flower during course of opening.

FIG. 6 Open flower—plan view—obverse.

FIG. 7 Open flower—plan view—reverse.

FIG. 8 Fully open flower—plan view—obverse.

FIG. 9 Fully open flower—plan view—reverse.

Figures 10, 11, 12, 13, 14, 15, 16, 17, 18:
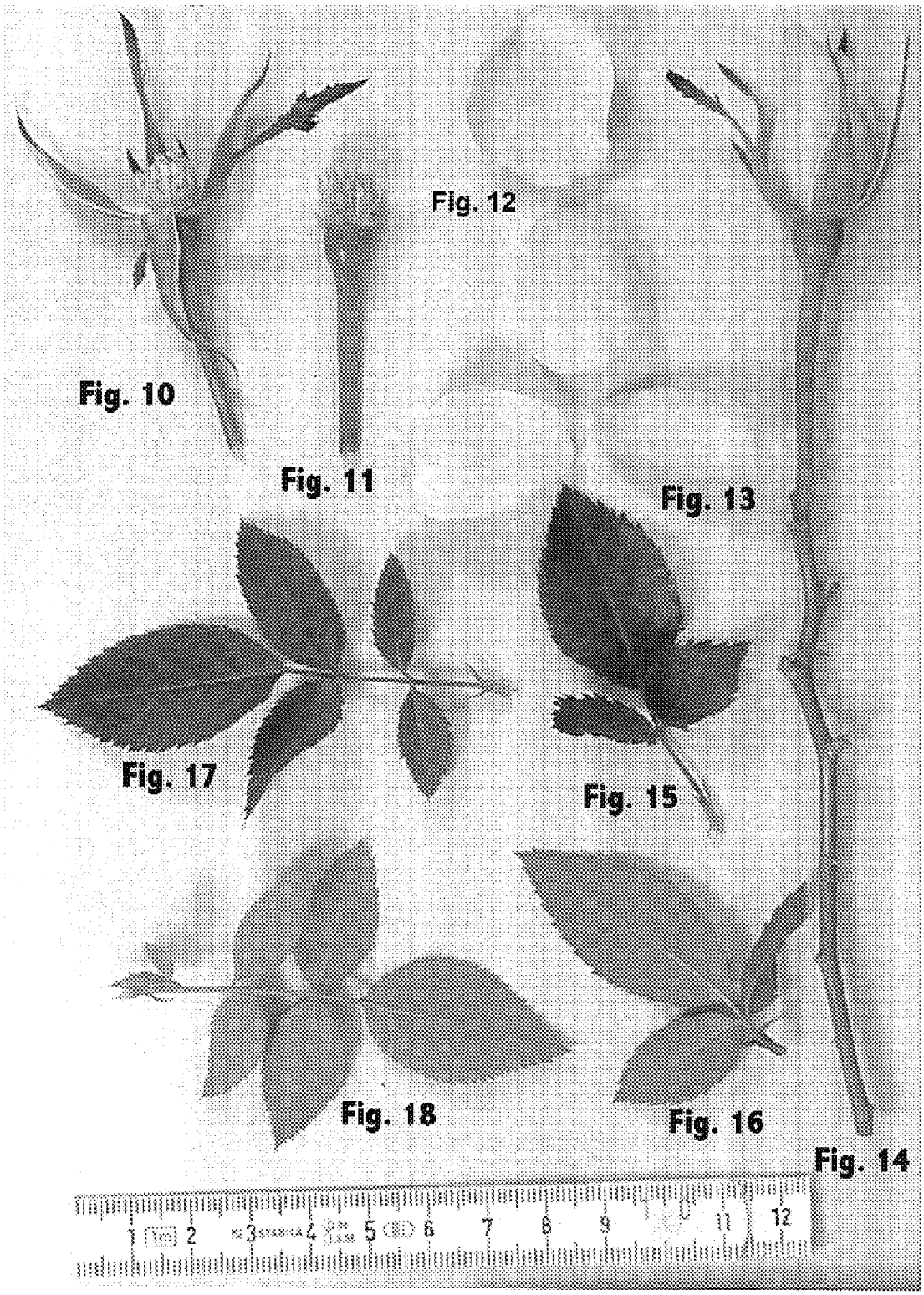

Photo sheet #2:

FIG. 10 Receptacle showing stamens and pistils.

FIG. 11 Receptacle showing stamens and pistils (sepals removed).

FIG. 12 Flower petals, detached—outer surface.

FIG. 13 Flower petals, detached—inner surface.

FIG. 14 Bare stem exhibiting thorns and flower attachment.

FIG. 15 Three leaflets upper side.

FIG. 16 Three leaflets reverse side.

FIG. 17 Five leaflets upper side.

FIG. 18 Five leaflets reverse side.

DETAILED BOTANICAL DESCRIPTION OF THE VARIETY

The following is a detailed description of the Miniature Rose: *Rosa hybrida* 'EVERgreen'.

The following observations, measurements, values and comparisons describe plants grown in glass houses in Faaborg, Denmark. The age of the observed plants where 11 to 13 weeks after propagation by cuttings, and produced as a flowering pot plants in container of 12 centimeter in diameter.

Color references are made using The Royal Horticultural Society (London, England) Colour Chart, 1995, except where common terms of color are used. For a comparison, the nearest existing rose variety is 'KORbritta', a rose variety described and illustrated in U.S. Plant Pat. No. ,11,146. Chart 1 details several physical characteristics of 'EVERgreen' and 'KORbritta'.

CHART 1

| | 'EVERgreen' | 'KORbritta' |
|---|---|---|
| Petal color, Upper surface | Yellow Group 12D | Yellow-Orange Group 21B |
| Petal color, Reverse surface | Yellow Group 12D | Yellow-Orange Group 21B |
| Petal count | 30–35 | 20–25 |

Parents: Unnamed seedling. Times. Unnamed seedling.
Classification:
Botanical: *Rosa hybrida.*
Commercial: Miniature.

PLANT

Plant growth: Moderately vigorous. Grows compact upright to bushy. When grown as 10 cm pot plant, the average height of the plant itself is 18 to 20 cm, and average with is 20 cm. When grown as a 15 cm pot plant, the average height of the plant itself is 22 to 27 cm, and average with is 30 cm. Production time is generally 11 to 13 weeks depending on average temperature, light level, and cultural practices.

STEM

Color:
*Young wood.*—Yellow-Green Group 146A. With intonations of Greyed-Purple Group 185A.
*Older wood.*—Yellow-Green Group 137A.
Thorns:
*Incidence.*—Low number of thorns.
*Size.*—2–3 mm.
*Color.*—Greyed-Red Group 179D.
*Shape.*—Deep concave.
Surface:
*Young wood.*—Smooth.
*Older wood.*—Smooth.
Stem diameter: 3–4 mm.
Internode length: 20–30 mm.
Numbers of internodes: 7–9.
Plant foliage: Leaves arranged alternately, compound with 3, 5 or 7 leaflets per leaf, generally symmetrical, abundant, and flat in aspect. Stipules at petiole base.
Quantity of leaves: 7–9 per lateral branch.
Leaf size. Medium 70–75 mm(l). times. 55–60 mm(w), for 5 leaflet.
Petioles:
*Color.*—Yellow-Green Group 146A, With intonations of Greyed-Purple Group 185A. Margins: with small prickles. Length: 10–20 mm Diameter: about 1–2 mm.
Stipules:
*Size.*—5–6 mm.
*Surface.*—Smooth.
*Color.*—Yellow-Green Group 146B, with intonations of Greyed-Purple Group 185A.
*Margins.*—Serrated, single.
Rachis:
*Color.*—Yellow-Green Group 146A, With intonations of Greyed-Purple Group 185A. Margins: Margins with small prickles. Length: 20 to 25 mm.
Leaflets:
*Edge.*—Serrated.
*Serration.*—Double.
*Shape.*—Ovate with acute apex and obtuse base.
*Texture.*—Smooth.
*Appearance.*—Glossy.
*Size.*—Length: 30 to 45 mm. With: 12 to 25 mm.
*Color.*—Young foliage: Upper surface: Yellow-Green Group 146A, with intonations of Greyed-Purple Group 183B. Edge color is Greyed-Purple Group 183B. Lower surface: Yellow-Green Group 147C, with intonations of Greyed-Purple Group 183B. Edge color is Greyed-Purple Group 183B.
*Color.*—Mature foliage: Upper surface: Green Group 136A Lower surface: Greyed-Green Group 191A.

INFLORESCENCE

Blooming habit: Recurrent.
Number of flowers. Generally 1 bud per flowering stem.
Peduncle:
*Color.*—Yellow-Green Group 144A.
*Texture.*—Smooth, with stipitate glands.
*Length.*—35–45 mm. Strength: Upright.
Receptacle:
*Surface.*—Smooth, glabrous.
*Shape.*—Funnel-shaped.
*Size.*—h: 6–7 mm. w: 7–8 mm.
*Color.*—Yellow-Green Group 144A.

Sepals:

*Quantity.*—5.

*Shape.*—Narrowly ovate w. acute tip.

*Texture.*—Leathery.

*Margin.*—Foliaceous appendages on 3 of the five sepals.

*Appearance.*—Dull.

*Color.*—Upper surface: Yellow-Green Group 146B–C, edge in Greyed-Purple Group 183D. Reverse surface: Yellow-Green Group 138B–C, edge in Greyed-Purple Group 183D.

Buds:

*Size.*—22–25 mm (h) 15–18 mm (w)upon opening.

*Shape.*—Pointed ovoid.

*Color.*—At ¼ opening, Yellow Group 12D, with intonations of Red Group 47C, and Green-Yellow Group 149C at the edges.

Flower:

Duration: As a pot plant, flowers last from 21 to 28 days.

*Fragrance.*—None.

*Size.*—45–60 mm in diameter.

*Form.*—Shape of flower when viewed from the side. Upon opening: Cupped. Open flower: Cupped.

*Color.*—Petals, upon opening. Upper surface: Yellow Group 12D, with intonations of Yellow-Green Group 149C. Reverse surface: Yellow-Green Group 149C, with intonations of Orange-Red Group 31B.

*Petals after opening.*—Upper surface: Yellow Group 12D, with intonations of Yellow-Green Group 149C at the edge. Reverse surface: Yellow-Green Group 149C, with intonations of Orange-Red Group 31B.

*Basal petals spots.*—Size 2–3 mm. Color: Yellow-Green Group 154B.

*General tonality.*—On Open flower: Third day: Greyed-Yellow Group 162B, with intonations of Yellow-Green Group 149C. Afterwards: Greyed-Yellow Group 162B, with intonations of Yellow-Green Group 149C.

Petals:

Petal reflex: Outermost petals reflex backwards at opening. Fully open all petals reflex backwards:

Texture: Smooth.

Petal edge: Uniform.

Petal count: Approximately 30–35 on the average per flower.

Petal size: Length 25–30 mm. Width 30–35 mm.

Shape:

*Outer petals.*—Round.

*Inner petals.*—Ovate.

Reproductive organs

Stamen number: Approximately 80–85 on average per flower.

Pollen:

*Color.*—Yellow-Orange Group 22A, Abundance: Average.

Anthers:

*Size.*—1–2 mm. Color: Yellow-Orange Group 22A, Shape: Oblong.

Filaments:

*Size.*—4–5 mm. Color: Yellow-Orange Group 14B.

Pistils number: Approximately 40–45 on average per flower.

Stigmas:

*Location.*—Under in location to anthers. Color: Yellow-Orange Group 14B.

Styles:

*Color.*—Yellow-Orange Group 15C. Length: 5 to 6 mm.

Development

Vegetation: Dense.

Blooming: Abundant.

Aptitude to bear fruit: Poor.

Resistance to diseases: Above average resistance to mildew and Botrytis under normal growing conditions in Faaborg, Denmark. Hips/seeds has not been observed due to that the plant has never been grown to the stage of seed development, due to the fact that the variety is developed for use as a flowering pot plant only.

Winter hardiness & drought/heat tolerance: Due to the fact that this variety is a potted flowering plant, developed for one time use only(indoor houseplant), the plant has not been tested for winter hardiness or drought/heat tolerance.

I claim:

1. A new and distinct variety of rose plant of the miniature class, substantially as herein illustrated and described as a distinct and novel rose variety due to its abundant, long lasting, warm yellow-lime colored flowers, attractive long lasting foliage, vigorous and compact growth, year round flowering under glasshouse conditions, suitability for production from softwood cuttings in pots, and durable flowers and foliage which make the variety suitable for distribution in the floral industry.

* * * * *